US008658807B2

(12) United States Patent
Hutchenson et al.

(10) Patent No.: US 8,658,807 B2
(45) Date of Patent: Feb. 25, 2014

(54) HYDROGENATION PROCESS FOR THE PREPARATION OF TETRAHYDROFURAN AND ALKYLATED DERIVATIVES THEREOF

(75) Inventors: Keith W. Hutchenson, Lincoln University, PA (US); Sourav Kumar Sengupta, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 218 days.

(21) Appl. No.: 13/262,837

(22) PCT Filed: Apr. 6, 2010

(86) PCT No.: PCT/US2010/030047
§ 371 (c)(1),
(2), (4) Date: Oct. 4, 2011

(87) PCT Pub. No.: WO2010/117986
PCT Pub. Date: Oct. 14, 2010

(65) Prior Publication Data
US 2012/0035378 A1  Feb. 9, 2012

Related U.S. Application Data

(60) Provisional application No. 61/167,413, filed on Apr. 7, 2009.

(51) Int. Cl.
*C07D 307/08* (2006.01)
(52) U.S. Cl.
USPC .......................................................... 549/429

(58) Field of Classification Search
USPC .......................................................... 549/429
See application file for complete search history.

(56) References Cited

U.S. PATENT DOCUMENTS 2,846,449 A    8/1958  Bandford

OTHER PUBLICATIONS

Tarbell et al., The Condensation of Sulfoxides With p-Toluenesulfonamide and Substituted Acetamides, Journal of the American Chemical Society 63, 1941, pp. 2939-2942.
Watson et al., Butaine-1,4-Diol From Hydrolytic Reduction of Furan, Ind. Eng. Chem. Prod. Res. Develop. 12, 1973, pp. 310-311.
Tetrahydrofuran. II. Kinetics of hydrogenation of furan. Wang, Jen; Yen, Chih-Knang; Li, Shih-Tsin. K'o Hsueh T'ung Pao (1958), 434-5. . CAN 53:62551 AN 1959:62551 CAPLUS.
Tetrahydrofuran. III. High pressure hydrogenation of furan. Wang, Jen; Yen, Chih-Knang; Li, Shih-Tsin. K'o Hsueh T'ung Pao (1958), 435-7. CAN 53:62552 AN 1959:62552 CAPLUS.
Li Ping et al., Preparation of THF Using Hydrogenation of Furan and Catalyzation of Raney Ni, Applied Science and Technology, vol. 35, No. 7, pp. 65-68, July 2008.
Zhao Huiji et al., Preparation of Tetrahydrofurfuryl Alcohol Using Hydrogenation of Furfuryl Alcohol Catalyzed by Raney Nickel Catalyst, Journal of the University of Petroleum, vol. 27, No. 1, pp. 91-94, Feb. 2003.

*Primary Examiner* — Taofiq A Solola

(57) ABSTRACT

A process is provided for the synthesis of tetrahydrofuran and related compounds by hydrogenation of furan and derivatives, using a sponge nickel catalyst that has been promoted with iron and chromium.

12 Claims, 3 Drawing Sheets

HYDROGENATION PROCESS FOR THE PREPARATION OF TETRAHYDROFURAN AND ALKYLATED DERIVATIVES THEREOF

TECHNICAL FIELD

This disclosure relates to the manufacture of tetrahydrofuran and related compounds, and to the industrial use thereof for the synthesis of other useful materials.

BACKGROUND

Tetrahydrofuran ("THF") and related compounds are useful as solvents and as intermediates in the preparation of industrial chemicals used as pharmaceuticals, herbicides and polymers. For example, tetrahydrofuran is used to make polytetramethylene glycol, which may in turn be used to make polyether ester elastomers and polyurethane elastomers.

"Sponge" metal catalysts such as Raney® nickel catalysts have been used to catalyze the hydrogenation of furan to produce tetrahydrofuran, as discussed e.g. in U.S. Pat. No. 2,846,449. In some instances, the catalyst has been promoted with a small amount of an additional catalytically-active metal such as chromium, as discussed in "Tetrahydrofuran II, Kinetics of Hydrogenation of Furan", Wang et al in *K'o Hsueh T'ung Pao* (1958) pages 434~5; and "Tetrahydrofuran III, High Pressure Hydrogenation of Furan", Jen et al in *K'o Hsueh T'ung Pao* (1958) pages 435~7.

There nevertheless remains a need for catalytic hydrogenation processes to produce tetrahydrofuran, and related compounds, that have greater commercial viability.

SUMMARY

The inventions disclosed herein include processes for the preparation of tetrahydrofuran, and related compounds, and for the preparation of products into which such tetrahydro (or substituted) furans can be converted, that are improved by catalyst selection.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination may be characterized by the absence of the features omitted to form the subcombination; (2) each of the features, individually, included within the combination of any described embodiment; and (3) other combinations of features formed by grouping only selected features taken from two or more described embodiments, optionally together with other features as disclosed elsewhere herein. Some of the specific embodiments of the processes hereof are as follows:

In one embodiment hereof, this invention provides a process for the synthesis of a compound as represented by the structure of the following Formula (I)

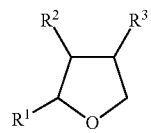

by contacting in a reaction mixture a compound as represented by the structure of the following Formula (II)

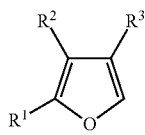

with hydrogen in the presence of a sponge nickel catalyst that comprises iron and chromium; wherein $R^1$, $R^2$, and $R^3$ are each independently selected from H and a $C_1$ to $C_4$ alkyl group.

In another embodiment hereof, a process is provided for preparing a Formula (I) product, as described above, that further includes a step of subjecting the product to a reaction (including a multi-step reaction) to prepare therefrom a compound (such as that useful as a monomer), oligomer or polymer.

An advantageous feature of the processeses hereof is the increased selectivity, lifetime and productivity of the sponge nickel catalysts selected for use herein.

DETAILED DESCRIPTION

Figure 1:
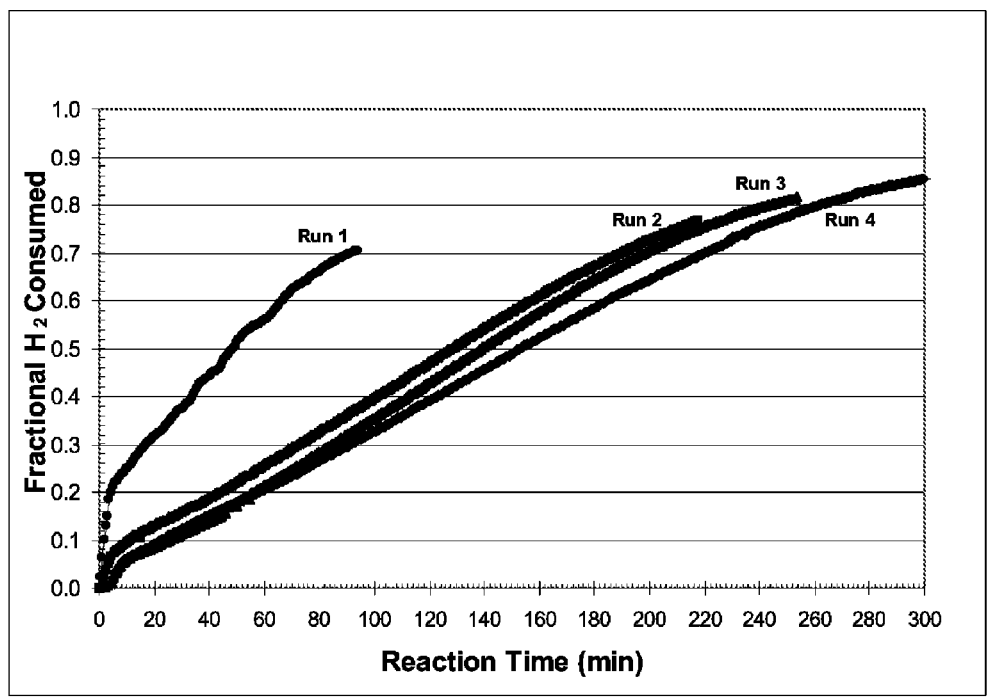
FIG. 1 illustrates the performance in Control A of an unpromoted sponge nickel catalyst over four successive runs in the hydrogenation of furan in a slurry reactor.

The inventions disclosed herein include processes for the preparation of tetrahydrofuran and processes for the preparation of products into which tetrahydrofuran can be converted.

In one embodiment hereof, this invention provides a process for the synthesis of a compound as represented by the structure of the following Formula (I)

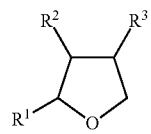

by contacting a compound as represented by the structure of the following Formula (II)

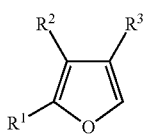

with hydrogen, in the presence of a sponge nickel catalyst that contains iron and chromium; wherein $R^1$, $R^2$, and $R^3$ are each independently selected from H and a $C_1$ to $C_4$ alkyl group, such as methyl, ethyl, propyl, butyl and any combination thereof.

In one embodiment of the processes hereof, $R^1$, $R^2$, and $R^3$ all equal H, in which case the Formula (I) product is tetrahydrofuran and the Formula (II) compound the starting material, is furan. The hydrogenation of furan to produce tetrahydrofuran may in such case be represented by the following equation:

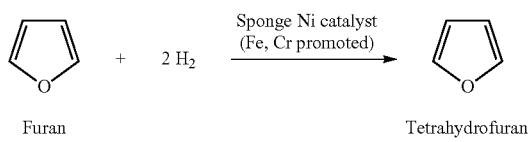 [SMILES: c1ccoc1 ; c1ccoc1]

In another embodiment, the Formula (II) compound used as the feed material in the processes hereof is obtained by the decarbonylation of a compound as represented by the structure of the following Formula (III):

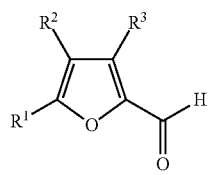

wherein $R^1$, $R^2$, and $R^3$ are defined as described above. In yet another embodiment of the processes hereof, $R^1$, $R^2$, and $R^3$ all equal H, in which case the compound of Formula (III) is furfural and the decarbonylation reaction may be represented by the following equation:

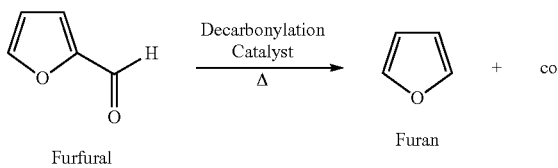

A decarbonylation reaction, and catalysts useful therein, are well known to the artisan.

In a further embodiment of the processes hereof, the compound of Formula (III) is derived from a biological material, which is typically a good source of hemicellulose. Examples of biological materials suitable for use herein for such purpose include, without limitation, straw, corn cobs, corn stalks/corn stover, sugar bagasse, hardwoods, cotton stalks, kenaf, oat hulls, and hemp. When a Formula (II) compound as feed material for the processes hereof is obtained from a Formula (III) compound, especially when it is furfural, the Formula (III) compound should be freshly distilled before use, since it can oxidize and change color, producing undesirable high-boiling oxidation products.

In the processes hereof, the hydrogenation reaction is catalyzed by a sponge nickel catalyst that includes iron and chromium along with nickel in the contents thereof. In such case, it is often said that the sponge nickel catalyst is promoted with or by iron and chromium. Sponge nickel catalysts as used herein, as do catalysts known as "skeletal" nickel catalysts, "skeleton" nickel catalysts and Raney® nickel catalysts, refer to metallic catalysts that are prepared by leaching out aluminum from an alloy of nickel and aluminum using aqueous alkali. The alloy is typically about 50% aluminum by weight before leaching, and the majority, but not all, of the aluminum is removed during leaching. The original process to prepare such porous nickel catalysts was discovered by Raney in 1925 with removal of silicon from a nickel/silicon alloy by an alkaline solution (as further discussed in U.S. Pat. No. 1,563,587). Raney later discovered that using nickel/aluminum alloys was an improvement over the nickel/silicon alloy (as further discussed in U.S. Pat. No. 1,628,190). Sponge metal catalysts can be prepared by leaching alloys of aluminum with other metals as well, e.g., cobalt, iron, copper, and others. The term "Raney" as a descriptor of sponge metal catalysts prepared by this process is a registered trademark of W.R. Grace & Co.

The sponge nickel catalysts used in the processes described herein contain small amounts of iron and chromium metals; that is, as aforesaid, the sponge nickel catalyst is promoted with or by iron and chromium. Such catalysts are prepared in the same manner as unpromoted sponge nickel catalysts, i.e. by forming an alloy of nickel, aluminum, chromium and iron and then using aqueous alkali to remove aluminum. In one embodiment, a sponge nickel catalyst as used herein may contain about 0.5% to about 6% iron by weight and/or about 0.5% to about 6% chromium by weight, based on the combined weight of all components of the catalyst together.

One example of a commercially available catalyst suitable for use in the processes hereof is Raney® 2400 Nickel, which is a product of W.R. Grace & Co. (Columbia, Md.). This is a sponge catalyst that contains 81.0 wt % or more nickel, 6.0-13.0 wt % aluminum, 2.0-3.0 wt % iron, and 2.0-3.0 wt % chromium [according to the manufacturer's information as reported by Sigma-Aldrich (St. Louis, Mo., USA)]. The Raney® 2400 Nickel catalyst is supplied in a slurry grade (i.e. a catalyst powder with particle size typically in the range 25-55 micrometers effective diameter), and a similar catalyst, Raney® 2486 Nickel, is also available in a fixed bed grade (i.e. catalyst pellets typically of a 3×8 standard mesh size).

Catalyst loading in the reactor may be in the amount of at least about 1 wt % or at least about 4 wt %, and yet in an amount of no more than about 15 wt % or no more than about 12 wt %, catalyst relative to the amount of Formula (II) compound present on a dry basis. The reaction may be run in a solvent such as n-propanol, or excess Formula (I) compound may be used as a solvent. The reaction mixture may contain about 60 to about 80.0 wt % solvent. Formula (I) compound used as a solvent may be used in an amount of about 5 to about 10 times the amount that would be expected to be produced by the reaction being conducted.

The temperature of the hydrogenation reaction in the processes hereof may range from about 30° C. to about 150° C. In various embodiments, for example, the reaction temperature may range from about 100° C. to about 120° C. Depending on the choice of reactor to be used, the reaction temperature referred to here is, in certain embodiments, the temperature that has been provided for the catalyst in the catalyst zone of the reactor. A temperature in these ranges is provided, for example, by heating the various portions of the reactor from a source external thereto, in particular a heating element designed to surround and heat the catalyst zone of the reactor, and thus the catalyst itself. The selected temperature thus exists in the catalyst zone of the reactor upon the occasion when the compound of Formula (II) is contacted with the catalyst. In various other embodiments, the reactor may be equipped with an external cooling coil that is connected to a recirculating water bath, and an electrical heating jacket may be mounted around the reactor and cooling coil.

Alternatively, however, in other embodiments, the reaction can be conducted in an adiabatic reactor where the elevated reaction temperature of, for example, about 100° C. to about 120° C. is achieved by the exothermic heat of reaction.

The reaction is generally run at a hydrogen pressure of about 200 to about 2500 psig (1.4 to 17.2 MPa), and in one embodiment may be run at a hydrogen pressure of about 500 to 1000 psig (3.4 to 6.9 MPa). The pressure should be high enough to quickly saturate the liquid Formula (II) compound with hydrogen in the reactor. A setpoint hydrogen pressure may be maintained as a constant condition during the course of the reaction by supplying hydrogen from a high-pressure storage vessel via a pressure regulator.

Hydrogen is mixed in a reaction mixture with the Formula (II) compound in a ratio of about 2 to about 4 moles of hydrogen per mole of Formula (II) compound, i.e. from about a stoichiometric amount of hydrogen up to about a 100% molar excess of hydrogen. In another embodiment, hydrogen is mixed with the Formula (II) compound in a ratio of about 2.4 to about 3.0 moles of hydrogen per mole of Formula (II) compound, i.e. from about a 20% to about a 50% molar excess of hydrogen. Using a molar excess of hydrogen appears to help prevent catalyst deactivation. The reactor may be maintained at the prescribed temperature and pressure until the hydrogen consumption subsides, as evidenced by a steady pressure in the hydrogen supply vessel. Typical reaction times are on the order of one to three hours.

Reactors suitable for use in the processes hereof include stirred slurry reactors; fluidized bed reactors; and fixed-bed reactors, and pipe, tubular or other plug-flow reactors (and the like) in which the catalyst particles are held in place and do not move with respect to a fixed residence frame. Reactants may be flowed into and through reactors such as these on a continuous basis to give a corresponding continuous flow of product at the downstream end of the reactor. These and other suitable reactors are more particularly described, for example, in Fogler, *Elements of Chemical Reaction Engineering,* 2nd Edition, Prentice-Hall Inc. (1992). The hydrogenation reaction can be run continuously or in batch mode. Ordinarily, it is run continuously.

The process may also involve purifying the Formula (I) product by a further step such as distillation. The Formula (I) product may be fed, for example, into a distillation column to remove unreacted Formula (II) compound and other impurities that may be present, and the distilled product can then be isolated and recovered.

The product may also, however, be subjected with or without recovery from the reaction mixture to further steps to convert it to another product such as another compound (such as a type useful, for example, as a monomer), or an oligomer or a polymer. Another embodiment of a process hereof thus provides a process for converting the Formula (I) product, through a reaction (including a multi-step reaction), into another compound, or into an oligomer or a polymer. For example, the Formula (I) product tetrahydrofuran may be made from the Formula (II) compound furan by a process such as described above, and then used for the preparation of polytetramethylene ether glycol, which in turn can be reacted with 1,4-butanediol and terephthalic acid to produce polyetherester elastomers, or with diisocyanates to produce polyurethanes. Processes suitable fo the preparation of products such as those named above are well known to the artisan.

EXAMPLES

The advantageous attributes and effects of the processes hereof may be more fully appreciated from a series of examples (Examples 1~2), as described below. The embodiments of these processes on which the examples are based are representative only, and the selection of those embodiments to illustrate the invention does not indicate that reactants, components, materials, conditions, specifications and/or techniques not described in these examples are not suitable for practicing these processes, or that subject matter not described in these examples is excluded from the scope of the appended claims and equivalents thereof. The significance of the examples is better understood by comparing the results obtained therefrom with the results obtained from a trial run (Control A) that is designed to serve as a controlled experiment and provide a basis for such comparison in respect of the fact that the catalyst used therein did not contain iron or chromium.

Materials.

The following materials were used in the examples: Furan (CAS #110-00-9, >99% purity), 1-propanol (CAS#71-23-8, 99.5% purity), and hexadecane (CAS #544-76-3, 99% purity), which were obtained from Sigma-Aldrich Inc. (St. Louis, Mo., USA) and used as received without further purification; and tetrahydrofuran (CAS #109-99-9, anhydrous, >99.9% purity), which was obtained from Sigma-Aldrich Inc. (Sheboygan, Wis., USA) and used as received without further purification.

The following sponge nickel catalysts were obtained from W.R. Grace & Co. (Columbia, Md., USA):
  Raney® 2400 Nickel, a slurry grade sponge nickel catalyst promoted with iron and chromium;
  Raney® 2800 Nickel, a slurry grade sponge nickel catalyst;
  Raney® 2486 Nickel, a fixed-bed grade sponge nickel catalyst promoted with iron and chromium; and
  Raney® 5886 Nickel, a fixed-bed grade sponge nickel catalyst.

Abbreviations.

The meaning of abbreviations as used in the example is as follows: "cm" means centimeter(s), "FID" means flame ionization detector, "g" means gram(s), "GC" means gas chromatography, "gmol" means gram mole(s), "mL" means milliliter(s), "mol %" means mole percent, "MPa" means megapascal(s), "rpm" means revolutions per minute, "THF" means tetrahydrofuran, and "wt %" means weight percent.

The processes hereof advantageously provide an increased selectivity to, and yield of, the desired Formula (I) compound product as compared to known processes. As used herein, the term "selectivity" for a product ("P") denotes the molar fraction or molar percentage of P in the final product mix, and the term "conversion" denotes how much reactant was used up as a fraction or percentage of the theoretical amount. The conversion multiplied by the selectivity thus equals the maximum "yield" of P, while the actual yield, also referred to as "net yield," will normally be somewhat less than this because of sample losses incurred in the course of activities such as isolating, handling, drying, and the like. As used herein, the term "purity" denotes what percentage of the in-hand, isolated sample is actually the specified substance.

General Method for Example 1 and Control A

Example 1 and Control A were conducted in a 50-mL Microclave® autoclave (from Autoclave Engineers) configured as an agitated batch slurry reactor. The reactor was equipped with a gas entrainment agitator and a flat blade impeller operating at about 800 rpm. The reactor was also equipped with an external cooling coil which was connected to a recirculating water bath operated at 15° C. An electrical heating jacket was mounted around the reactor and cooling coil.

The reactor, furan, and reaction solvent (n-propanol) were chilled overnight in a refrigerator due to the volatility of the furan. A reactor feed solution consisting of furan, n-hexadecane (used as an internal standard for offline GC analysis) and n-propanol (solvent) was prepared in advance of charging the reactor. This solution contained approximately 29.4 wt % furan, 0.6 wt % n-hexadecane and 70.0 wt % n-propanol. Chilled reactor feed and water-wet catalysts were charged to the reactor at a catalyst loading of about 5 wt % catalyst relative to furan on a dry basis, and the catalysts were reduced in situ during the course of the reactions.

After charging the contents and chilling the reactor, the reactor headspace was flushed with three successive hydrogen flushes of about 3 bar (0.3 MPa) each. The reactor was then charged with about 60 bar (6.0 MPa) of hydrogen and isolated to monitor for any reactor leaks. Agitation was then begun at about 800 rpm, the cooling water flow was stopped, and the temperature controller was activated to initiate heating.

As the reactor temperature approached the setpoint temperature of 120° C., the reactor was opened to a pressure regulated hydrogen supply from a calibrated volume and adjusted to the setpoint pressure of 70 bar (7.0 MPa). The reaction was conducted at about 120° C. under a constant total pressure of hydrogen of about 70 bar (7.0 MPa). This pressure was maintained during the course of the reaction by supplying hydrogen from a high-pressure storage vessel via a pressure regulator. The reactor was maintained at the prescribed temperature and pressure until the hydrogen consumption subsided, as evidenced by a steady pressure in the hydrogen supply vessel. Typical reaction times were on the order of one to three hours.

When the reaction was complete, the temperature controller was deactivated and the cooling water was valved into the reactor cooling coil. After the reactor had cooled to about 15° C., the reactor was disconnected from the head assembly, and the reaction products and used catalyst were recovered. A sample of this reaction product was analyzed offline by gas chromatography.

Example 1

This reaction demonstrates the performance of a Fe, Cr-promoted nickel sponge metal catalyst in a slurry reactor.

A 50 mL stirred batch autoclave reactor was charged with a solution of 9.6 g of furan (CAS #110-00-9), 0.48 g hexadecane (CAS #544-76-3) in 21.1 g n-propanol (CAS #71-23-8) and 0.452 g of a powder iron and chromium promoted sponge nickel catalyst (Raney® Nickel 2400 from W.R. Grace), and the hydrogenation reaction was conducted as described above. Following this reaction, the reaction mixture was removed from the reactor via a dip tube equipped with a 2-micron sintered metal filter, thus retaining the catalyst in the reactor. The reactor was flushed three times with 25 mL of n-propanol, each flush being removed through the dip tube. The reactor was then recharged with a fresh solution of furan, hexadecane, and n-propanol, and the reaction was repeated. This process was repeated for a total of five successive reactions using the same catalyst charge.

Figure 2:
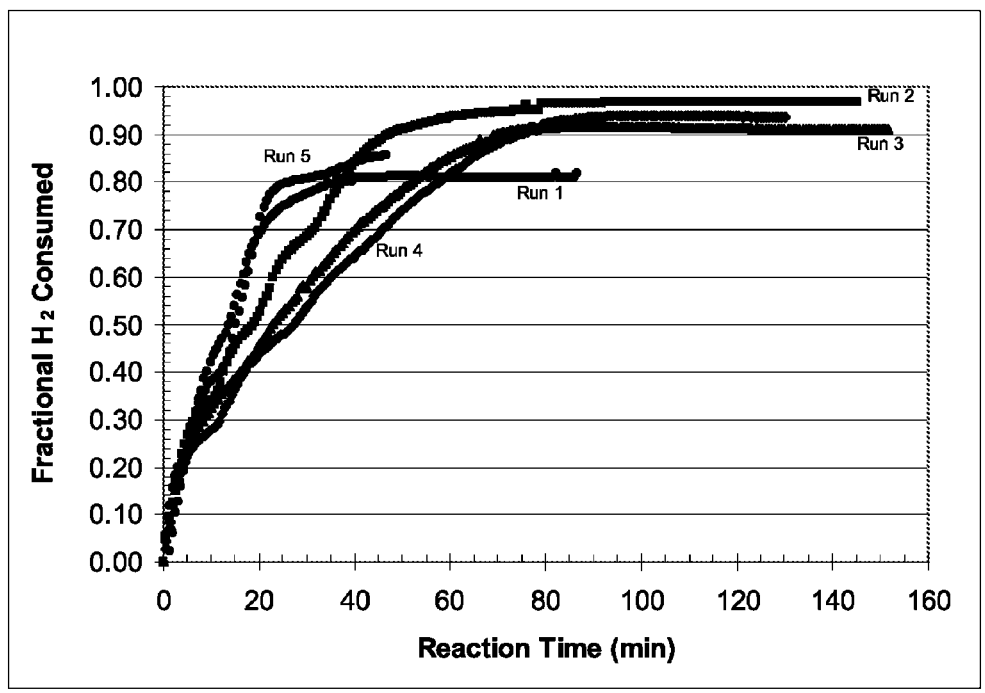
FIG. 2 illustrates the performance in Example 1 of a Fe, Cr-promoted sponge nickel catalyst over five successive runs in the hydrogenation of furan in a slurry reactor.

Product analysis by gas chromatography (GC-FID) using the hexadecane as an internal standard was used to determine the composition of the reactant and products in the recovered reaction mixture for each of these successive experiments, and the initial rate of reaction was calculated from the hydrogen consumption. Results are summarized in Table 1. FIG. 2 shows the consumption of hydrogen over the course of the five reactions, plotted as the fraction of hydrogen consumed relative to the theoretical amount required for complete hydrogenation of the furan charged to the reactor. The initial reaction rate is relatively stable over these successive runs, showing the benefit of the promoting iron and chromium metals in this sponge nickel catalyst versus an unpromoted sponge nickel catalyst, as is shown below in Control A.

TABLE 1

| Run | Furan Conversion (%) | THF Selectivity (%) | n-Butanol Selectivity (%) | Initial Reaction Rate (gmol $H_2$/min-g catalyst) |
| --- | --- | --- | --- | --- |
| 1 | 99.3 | 97.1 | 2.9 | 0.0334 |
| 2 | 99.8 | 98.2 | 1.8 | 0.0306 |
| 3 | 99.9 | 98.3 | 1.7 | 0.0311 |
| 4 | 99.9 | 98.5 | 1.5 | 0.0307 |
| 5 | 99.7 | 98.7 | 2.3 | 0.0369 |

Control A

This reaction demonstrates the performance of an unpromoted nickel sponge metal catalyst in a slurry reactor.

A 50 mL stirred batch autoclave reactor was charged with a solution of 8.7 g of furan (CAS #110-00-9), 0.43 g hexadecane (CAS #544-76-3) in 21.1 g n-propanol (CAS #71-23-8) and 0.456 g of a powder sponge nickel catalyst (Raney® Nickel 2800 from W.R. Grace), and the hydrogenation reaction was conducted as described above. Following this reaction, the reaction mixture was removed from the reactor via a dip tube equipped with a 2-micrometer sintered metal filter, thus retaining the catalyst in the reactor. The reactor was flushed three times with 25 mL of n-propanol, each flush being removed through the dip tube. The reactor was then recharged with a fresh solution of furan, hexadecane, and n-propanol, and the reaction was repeated. This process was repeated for a total of four successive reactions using the same catalyst charge.

Product analysis by gas chromatography (GC-FID) using the hexadecane as an internal standard was used to determine the composition of the reactant and products in the recovered reaction mixture for each of these successive experiments, and the initial rate of reaction was calculated from the hydrogen consumption. Results are summarized in Table 2. FIG. 1 shows the consumption of hydrogen over the course of the four reactions, plotted as the fraction of hydrogen consumed relative to the theoretical amount required for complete hydrogenation of the furan charged to the reactor. For this catalyst there is a rapid decline in initial reaction rate following the first 2-3 minutes of reaction for each of the four reactions. In addition, there is a significant decline in catalyst activity between Runs 1 and 2, and there is a continuing but smaller decline in catalyst activity (i.e. reaction rate) with subsequent runs.

TABLE 2

| Run | Furan Conversion (%) | THF Selectivity (%) | n-Butanol Selectivity (%) | Initial Reaction Rate (gmol $H_2$/min-g catalyst) |
|---|---|---|---|---|
| 1 | 97.0 | 98.1 | 1.9 | 0.0293 |
| 2 | 92.9 | 99.3 | 0.7 | 0.0091 |
| 3 | 97.0 | 100.0 | 0.0 | 0.0032 |
| 4 | 99.2 | 100.0 | 0.0 | 0.0058 |

Example 2

This reaction demonstrates the performance of a Fe, Cr-promoted nickel sponge metal catalyst, compared with an unpromoted nickel sponge metal catalyst, in a fixed bed reactor.

Figure 3:
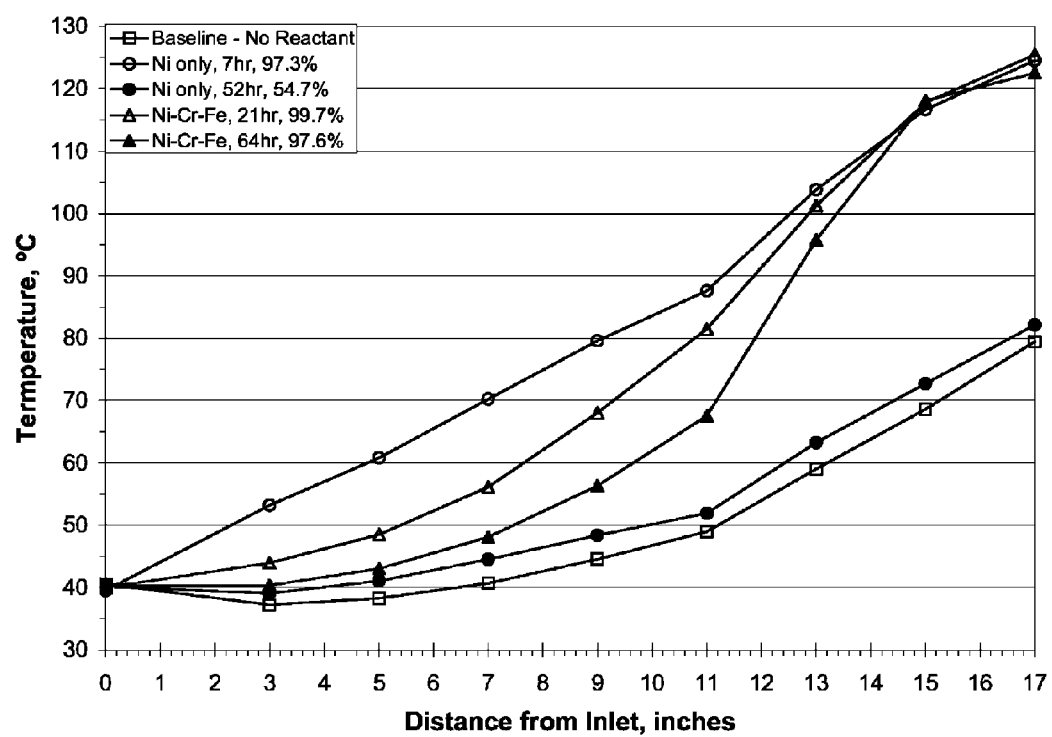
FIG. 3 illustrates the performance in Example 2 of an unpromoted sponge nickel catalyst and a Fe, Cr-promoted sponge nickel catalyst in the hydrogenation of furan in a fixed bed reactor.

This reaction was conducted at larger scale in a continuous up-flow packed bed reactor with a constant heat input to the system at a set mass flow rate. The total liquid flow rate through the reactor was 20 g/min, with 1.8 g/min of that flow being furan and the balance being THF as a diluent. In addition a 50 mol % excess of hydrogen was fed to the reactor. The liquid and gas feeds were preheated to the inlet temperature prior to reaching the reactor. With no reactant flow through the system, only diluent, the steady state baseline temperature profile (FIG. 3) was observed. The initial steady state exotherm with an unpromoted sponge nickel pellet catalyst (Raney® Nickel 5886 from W.R. Grace) after seven hours on-stream is shown in FIG. 3; the corresponding conversion level was 97%. After 52 hours of operation, the conversion level had decreased to just under 55%. This decrease in conversion can also be observed in the relative temperature profiles (FIG. 3).

On repeating these reaction conditions with an iron and chromium-promoted sponge nickel pellet catalyst (Raney® Nickel 2486 from W.R. Grace), the steady state experiments showed an exotherm with better than 99% conversion after 21 hours on-stream. While the overall profile was different than with the unpromoted Ni case, the outlet temperatures were the same indicating similar furan conversion. This high level of activity was maintained over 64 hours at a similarly high level of conversion of over 97%.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

Further in this specification, unless explicitly stated otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

What is claimed is:

1. A process for the synthesis of a compound as represented by the structure of the following Formula (I)

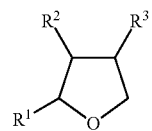

comprising contacting in a reaction mixture a compound as represented by the structure of the following Formula (II)

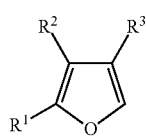

with hydrogen in the presence of a sponge nickel catalyst that comprises iron and chromium; wherein $R^1$, $R^2$, and $R^3$ are each independently selected from H and a $C_1$ to $C_4$ alkyl group.

2. A process according to claim 1 wherein $R^1$, $R^2$, and $R^3$ are each H.

3. A process according to claim 1 wherein the reaction mixture comprises hydrogen and Formula (II) compound in a ratio of between about 2.0 and about 4.0 moles of hydrogen per mole of Formula (II) compound.

4. A process according to claim 1 wherein the reaction mixture comprises hydrogen and Formula (II) compound in a ratio of between about 2.4 and about 3.0 moles of hydrogen per mole of Formula (II) compound.

5. A process according to claim 1 comprising feeding hydrogen to the reaction mixture at a pressure in the range of from about 200 to about 2500 psig.

6. A process according to claim 1 comprising feeding hydrogen to the reaction mixture at a pressure in the range of from about 500 to about 1000 psig.

7. A process according to claim 1 wherein the sponge nickel catalyst comprises iron in an amount of from about 0.5 to about 6 wt %.

8. A process according to claim 1 wherein the sponge nickel catalyst comprises chromium in an amount of from about 0.5 to about 6 wt %.

9. A process according to claim 1 wherein the reaction mixture has a temperature in the range of from about 30° C. to about 150° C.

10. A process according to claim 1 further comprising a step of decarbonylating a compound as represented by the structure of the following Formula (III)

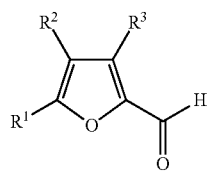

to provide the Formula (II) compound.

11. A process according to claim 10 wherein the compound of Formula (III) is derived from a biological material which is selected from the group consisting of: straw, corn cobs, corn stalks/corn stover, sugar bagasse, hardwoods, cotton stalks, kenaf, oat hulls, and hemp.

12. A process according to claim 1 further comprising a step of subjecting the Formula (I) compound to a reaction to prepare therefrom a compound, oligomer or polymer.

* * * * *